United States Patent
Lunkwitz et al.

(10) Patent No.: US 6,784,296 B2
(45) Date of Patent: Aug. 31, 2004

(54) PREPARATION OF TERPYRIDINES

(75) Inventors: Ralph Lunkwitz, Neustadt (DE); Gunther Pabst, Mannheim (DE); Günter Scherr, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/134,626

(22) Filed: Apr. 30, 2002

(65) Prior Publication Data

US 2003/0153761 A1 Aug. 14, 2003

(30) Foreign Application Priority Data

May 7, 2001 (DE) .......................... 101 22 025

(51) Int. Cl.$^7$ .......................................... C07D 401/02
(52) U.S. Cl. ...................................................... 546/258
(58) Field of Search ........................................ 546/258

(56) References Cited

PUBLICATIONS

F. R. Heirtzler, Synlett, No. 8, XP–002934351, pps. 1203–1206, "Preparation of Non–Symmetrical 2,3–Bis–(2, 2'–Oligopyridyl)Pyrazines via 1,2–Disubstituted Ethanones," 1999.

D. Guay, et al., Bioorganic & Medicinal Chemistry Letters 8, pps. 453–458, "A Series of Non–Quinoline cysLT$_1$ Receptor Antagonists: Sar Study on Pyridyl Analogs of Singular,"1998.

R–A. Fallahpour, Synthesis, No. 12, pp. 1665–1667, "An Efficient and Easy Route to Trimethyl Derivatives of 2,2' : 6',2"—Terpyridine", 2000.

E. C. Constable et al., J. Chem. Soc. Dalton Trans., pp. 1405–1408, "Synthesis and Co–ordination Behaviour of 6',6"—Bis (2–Pyridyl)—2,2':4,4":2,"—Quaterpyridein; 'Back–to–Back'2,2 : 6',2"—Terpyridine", 1990.

R. L. Frank, et al., J. AM. Chem. Soc., vol. 72, pp. 4182–4183, "Pyridines. VI. Polypyridyls by the Chichibabin Synthesis", Sep. 1950.

Primary Examiner—Zinna Northington Davis
(74) Attorney, Agent, or Firm—Oblon, Spivak, McClelland, Maier & Neustadt, P.C.

(57) ABSTRACT

The present invention provides a process for preparing a terpyridine compound of the formula I

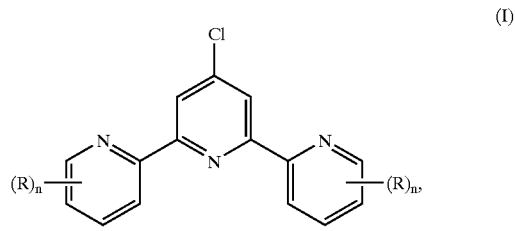

by obtaining a $C_1$–$C_4$-alkyl pyridine-2-carboxylate derivative by acid hydrolysis of a 2-cyanopyridine derivative by means of an anhydrous inorganic acid or its anhydride in the presence of water and a $C_1$–$C_4$-alkanol, with an equimolar amount of water being added to the 2-cyanopyridine derivative prior to addition of the anhydrous inorganic acid or its anhydride, subsequently condensing the resultant $C_1$–$C_4$-alkyl pyridine-2-carboxylate derivative with acetone in an aprotic solvent in the presence of a base, then reacting the obtained 1,5-bis(2-pyridyl)pentane-1,3,5-trione derivative with ammonia or ammonium salts $(NH_4)_qY$ with removal of the water of reaction formed by employing a $C_1$–$C_4$-alkanol as an entrainer, and finally chlorinating the resultant 2,6-bis (2-pyridyl)-4(1H)pyridinone derivative in the presence of phosphorus oxide chloride.

9 Claims, No Drawings

PREPARATION OF TERPYRIDINES

The present invention relates to a process for preparing terpyridines of the formula I

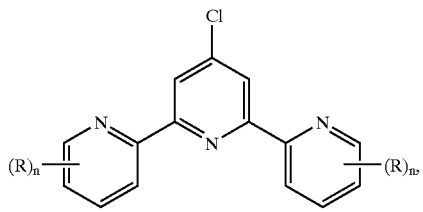

in which
- R are hydrogens or identical $C_1$–$C_{12}$-alkyl or $C_1$–$C_{12}$-alkoxy radicals and
- n is 0, 1, 2, 3 or 4 and is the same for both sets of radicals by successive reaction steps comprising
- A) condensation of a $C_1$–$C_4$-alkyl pyridine-2-carboxylate derivative with acetone in an aprotic solvent in the presence of a base,
- B) reaction of the 1,5-bis(2-pyridyl)pentane-1,3,5-trione derivative obtained in reaction step A with ammonia or ammonium salts $(NH_4)_qY$ with removal of the water of reaction formed, where the variable Y in $(NH_4)_qY$ is the anion of the parent q-basic acid $H_qY$ of the ammonium salt, and
- C) chlorination of the 2,6-bis(2-pyridyl)-4(1H)pyridinone derivative obtained in reaction step B,
  wherein the reaction step A is preceded by a reaction step A' in which the $C_1$–$C_4$-alkyl pyridine-2-carboxylate derivative is obtained by
- A') acid hydrolysis of a 2-cyanopyridine derivative by means of an anhydrous inorganic acid or its anhydride in the presence of water and a $C_1$–$C_4$-alkanol, with an equimolar amount of water being added to the 2-cyanopyridine derivative of the formula a prior to addition of the anhydrous inorganic acid or its anhydride, the base used in reaction step A is an alkali metal $C_1$–$C_4$-alkoxide or alkaline earth metal $C_1$–$C_4$-alkoxide,
the removal of the water of reaction in reaction step B is carried out using a $C_1$–$C_4$-alkanol as entrainer
and
the chlorination of the 2,6-bis(2-pyridyl)-4(1H)pyridinone derivative of the formula c in reaction step C is carried out using phosphorus oxide chloride ($POCl_3$) or using a mixture comprising phosphorus oxide chloride and at least one organic solvent selected from the group consisting of toluene, o-xylene, m-xylene and p-xylene.

The present invention further relates to a process for preparing $C_1$–$C_4$-alkyl pyridine-2-carboxylate derivatives from 2-cyanopyridine derivatives, to a process for preparing 1,5-bis(2-pyridyl)pentane-1,3,5-trione derivatives by condensation of a $C_1$–$C_4$-alkyl pyridine-2-carboxylate derivative with acetone, to a process for preparing 2,6-bis(2-pyridyl)-4(1H)pyridinone derivatives by reaction of a 1,5-bis(2-pyridyl)pentane-1,3,5-trione derivative with ammonia or ammonium salts and to a process for preparing terpyridines of the formula I by chlorination of a 2,6-bis(2-pyridyl)-4(1H)pyridinone derivative.

The interest in oligopyridines is tremendous, particularly because they are excellent complexing agents for metals. As a result, a wide variety of synthetic routes have been employed for these compounds. A review is given, for example, by R. -A. Fallahpour in Synthesis 2000, No. 12, 1665–1667.

The synthesis of 4'-chloro-2,2':6',6"-terpyridine from ethyl pyridine-2-carboxylate via the intermediates 1,5-bis (2-pyridyl)pentane-1,3,5-trione and 2,6-bis(2-pyridyl)-4 (1H)pyridinone is described by E. C. Constable and M. D. Ward in J. Chem. Soc. Dalton Trans. 1990, 1404–1409 (1). The condensation of the pyridinecarboxylic ester with acetone (corresponding to reaction step A of the process of the present invention) is carried out in the presence of sodium hydride as base. The resulting pentane-1,3,5-trione is then reacted with ammonium acetate under reflux to form the corresponding 4(1H)pyridinone (corresponding to reaction step B of the process of the present invention), which then reacts with an excess of phosphorus pentachloride in phosphorus oxide chloride as solvent to give the desired terpyridine (corresponding to reaction step C of the process of the present invention). The respective yields of the reactions corresponding to the reaction steps A, B and C are said by the authors to be 80%, 80% and 62%, respectively, which corresponds to an overall yield of terpyridine based on the pyridinecarboxylic ester used of about 40%.

According to R. L. Frank and E. F. Riener, J. Am. Chem. Soc., Vol. 72, 4182–4183 (2), ethyl picolinate (ethyl pyridine-2-carboxylate) is prepared by reacting 2-cyanopyridine with ethanol saturated with HCl gas. The imino ester formed as intermediate is then hydrolyzed to the ethyl ester by pouring into water. The yield of this reaction is said to be 40%.

Serious disadvantages of the procedure described in (1) are the use of extremely air- and moisture-sensitive sodium hydride and of large amounts of corrosive and toxic phosphorus pentachloride or phosphorus oxide chloride and the generally high starting material costs for pyridinecarboxylic esters. For these reasons, this route to terpyridines can be employed only with great difficulty, if at all, on a (large) industrial scale.

An attractive starting material for the synthesis of terpyridines is 2-cyanopyridine, because of the price advantage over pyridinecarboxylic esters. 2-Cyanopyridine can be converted as described in (2) into ethyl pyridinecarboxylates, but the synthesis described in (2) has the disadvantage that, based on the amount of 2-cyanopyridine used, only a small yield of the desired ester is obtained, which cancels out the price advantage. If the yield reported in (2) is multiplied by the yield of about 40% indicated above, the overall yield of terpyridine starting from 2-cyanopyridine is only about 16%. This is prohibitively low for (large-scale) industrial processes.

It is an object of the present invention to provide an inexpensive process for preparing terpyridines from 2-cyanopyridine which can be carried out on a (large) industrial scale and is acceptable from the points of view of occupational hygiene and the environment.

We have found that this object is achieved by a process for preparing terpyridines of the formula I

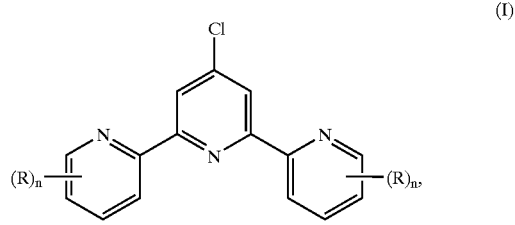

in which
R are hydrogens or identical $C_1$–$C_{12}$-alkyl or $C_1$–$C_{12}$-alkoxy radicals and
n is 0, 1, 2, 3 or 4 and is the same for both sets of radicals R,
by successive reaction steps comprising
A) condensation of a $C_1$–$C_4$-alkyl pyridine-2-carboxylate derivative of the formula a

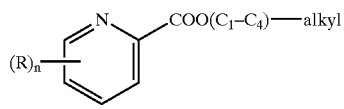
(a)

with acetone in an aprotic solvent in the presence of a base,
B) reaction of the 1,5-bis(2-pyridyl)pentane-1,3,5-trione derivative of the formula b

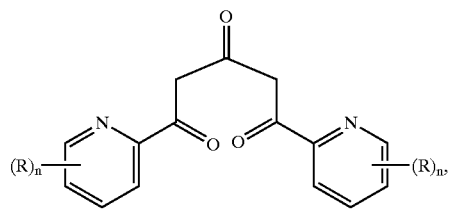
(b)

obtained in reaction step A with ammonia or ammonium salts $(NH_4)_qY$ with removal of the water of reaction formed, where the variable Y in $(NH_4)_qY$ is the acid anion of the parent q-basic acid $H_qY$ of the ammonium salt, and
C) chlorination of the 2,6-bis(2-pyridyl)-4(1H)pyridinone derivative of the formula c obtained in reaction step B

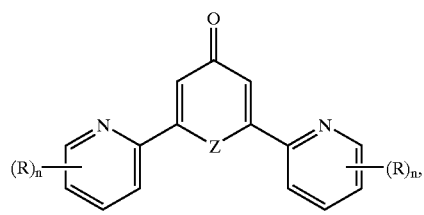
(c)

where Z is NH in the case of a reaction with ammonia in reaction step B and is $NH_2^{\oplus}[Y_{1/q}]^{\ominus}$ in the case of a reaction with ammonium salts $(NH_4)_qY$ in reaction step B,
wherein
the reaction step A is preceded by a reaction step A' in which the $C_1$–$C_4$-alkyl pyridine-2-carboxylate derivative of the formula a is obtained by
A') acid hydrolysis of a 2-cyanopyridine derivative of the formula a'

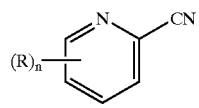
(a')

by means of an anhydrous inorganic acid or its anhydride in the presence of water and a $C_1$–$C_4$-alkanol, with an equimolar amount of water being added to the 2-cyanopyridine derivative of the formula a' prior to addition of the anhydrous inorganic acid or its anhydride,
the base used in reaction step A is an alkali metal $C_1$–$C_4$-alkoxide or alkaline earth metal $C_1$–$C_4$-alkoxide,
the removal of the water of reaction in reaction step B is carried out using a $C_1$–$C_4$-alkanol as entrainer
and
the chlorination of the 2,6-bis(2-pyridyl)-4(1H)pyridinone derivative of the formula c in reaction step C is carried out using phosphorus oxide chloride ($POCl_3$) or using a mixture comprising phosphorus oxide chloride and at least one organic solvent selected from the group consisting of toluene, o-xylene, m-xylene and p-xylene.

In formula a, $C_1$–$C_4$-alkyl radicals are methyl, ethyl, n-propyl, i-propyl, n-butyl, i-butyl, sec-butyl and tert-butyl, so that the corresponding $C_1$–$C_4$-alkanols with which the 2-cyanopyridines of the formula a' are reacted to form the compounds of the formula a are methanol, ethanol, n-propanol, i-propanol, n-butanol, i-butanol, sec-butanol and tert-butanol.

The latter listing also encompasses the $C_1$–$C_4$-alkanols which are used in reaction step B as entrainers for removing the water of reaction. The alkanols used in steps A' and B do not necessarily have to be identical.

$C_1$–$C_{12}$-Alkyl radicals R in the formulae I, a, b, c and a' can be, in addition to the abovementioned $C_1$–$C_4$-alkyl radicals, pentyl, sec-pentyl, tert-pentyl, neopentyl, 2,3-dimethyl-2-butyl, hexyl, 2-methylpentyl, heptyl, 2-methylhexyl, 2-ethylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl, (the names isooctyl, isononyl and isodecyl are trivial names and are derived from the carbonyl compounds obtained in the oxo process; cf. Ullmann's Encyclopedia of Industrial Chemistry, 5th Edition, Vol. Al, pages 290–293, and Vol. Alo, pages 284 and 285).

$C_1$–$C_{12}$-Alkoxy radicals R in the formulae I, a, b, c and a' and the $C_1$–$C_4$-alkoxide radicals of the alkali metal or alkaline earth metal alkoxides to be used as bases in step A are derived from the abovementioned $C_1$–$C_{12}$-alkyl or $C_1$–$C_4$-alkyl radicals.

To convert the 2-cyanopyridine derivative of the formula a' into the corresponding $C_1$–$C_4$-alkyl pyridine-2-carboxylate of the formula a, the former is usually dissolved or suspended in an excess of the corresponding absolute $C_1$–$C_4$-alkanol, admixed with the equivalent amount of water, based on the number of moles of the compound of the formula a', and the anhydrous inorganic acid is added, if appropriate a little at a time. It is naturally also possible to use alkanols with their typical residual water contents, in which case the amount of water is then reduced correspondingly.

The molar ratio of 2-cyanopyridine derivative to inorganic acid is usually from 1:4 to 1:10, and that of 2-cyanopyridine derivative to $C_1$–$C_4$-alkanol is usually from 1:15 to 1:40.

The reaction conditions in reaction step A' are usually chosen in a manner analogous to the conditions in the Pinner reaction leading to the imino esters, i.e. the inorganic acid is added at room temperature or slightly elevated temperature, which normally results in a further temperature increase due to the exothermic character of the reaction. The mixture is then usually allowed to react to completion under reflux.

The crude product obtained is generally worked up by distilling off the excess $C_1$–$C_4$-alkanol, taking up the residue in a suitable solvent and, to avoid possible hydrolysis of the ester formed, washing until neutral with the solution of a weak base, e.g. an aqueous sodium bicarbonate solution. After phase separation, the resulting solution of the product can, if a suitable aprotic solvent has been used, be processed further directly as described in step A or an appropriate solvent replacement has to be carried out beforehand.

Examples of anhydrous inorganic acids are anhydrous sulfuric acid, fuming sulfuric acid, anhydrous phosphoric acid, anhydrous pyrophosphoric acid and hydrogen chloride, with preference being given to using the latter.

Examples of anhydrides of these inorganic acids are sulfur trioxide and tetraphosphorus decaoxide.

As alkali metals or alkaline earth metals of the alkoxides in step A, particular mention may be made of sodium and potassium and also magnesium and calcium, especially sodium. Preference is accordingly given to using sodium $C_1$–$C_4$-alkoxides, in particular sodium methoxide.

Aprotic solvents which can be used in step A are generally well known to those skilled in the art. Examples are cyclic ethers such as tetrahydrofuran or dioxane, and also linear and branched glycol ethers which are obtainable from ethylene oxide and propylene oxide. Examples of such ethers are dimethoxyethane (DME) and further dimethyl ethers which are commercially available under the name Glyme®.

The reaction conditions in step A correspond to the usual conditions of the Claisen condensation, i.e. the reaction is normally carried out under reflux at the boiling point of the solvent used.

The molar ratio of ester derivative of the formula a to acetone is usually 2:1, corresponding to the stoichiometry of the reaction. In specific cases, slightly above or slightly below this ratio may be desirable.

The crude product obtained in step A is generally sufficiently pure and can therefore normally be used as starting material for reaction step B without elaborate purification. Thus, after adjusting the pH to a neutral or slightly acid value by means of a weak acid, e.g. acetic acid or the ammonium salt $(NH_4)_qY$ to be used in step B, the entrainer for step B can be added directly to the solution/suspension obtained in step A.

However, if higher purities are required, it is possible to separate off the aprotic solvent used in step A, dissolve or suspend the residue in water, add a weak acid, e.g. acetic acid, until the pH is neutral or slightly acid, filter off the usually solid reaction product with suction and wash it with a little water. If necessary, this can be followed by a drying step.

As solvent or suspension medium in reaction step B, use is made of the $C_1$–$C_4$-alkanol serving as entrainer. The molar ratio of trione derivative of the formula b to alkanol is usually from 1:75 to 1:125.

The removal of the water of reaction in reaction step B is carried out using customary methods of water separation. If the alkanol serving as entrainer has only limited miscibility with water, for instance in the case of the various $C_4$-alkanols, the water can be removed, for example, by discharging it after phase separation and the alkanol can be returned to the reaction mixture. If the alkanol and water have unlimited miscibility, the water can be separated off by distillation together with the alkanol and the latter can be worked up in a separate distillation step.

The reaction temperature in step B corresponds essentially to the customary temperatures in the refluxing $C_1$–$C_4$-alkanol/water mixture, with lower temperatures or temperature profiles also being able to be set at the beginning of the reaction.

Preferred entrainers in reaction step B are ethanol, n-propanol, i-propanol and n-butanol, with particular preference being given to ethanol.

Possible ammonium salts $(NH_4)_qY$ with which the trione obtained in step A is reacted in reaction step B are, for example, the ammonium salts of formic, acetic, carbonic, hydrochloric, sulfuric or phosphoric acid, i.e. $NH_4HCO_2$ (q=1, Y=$HCO_2^\ominus$), $NH_4CH_3CO_2$ (q=1, Y=$CH_3CO_2^\ominus$), $NH_4HCO_3$ (q=1, Y=$HCO_3^\ominus$)$(NH_4)_2CO_3$ (q=2, Y=$CO_3^{2\ominus}$), $NH_4Cl$ (q=1, Y=$Cl^\ominus$), $NH_4HSO_4$ (q=1, Y=$HSO_4^\ominus$), $(NH_4)_2SO_4$ (q=2, Y=$SO_4^{2\ominus}$), $NH_4H_2PO_4$ (Y=$H_2PO_4^\ominus$) und $(NH_4)_2HPO_4$ (q=2, Y=$HPO_4^{2\ominus}$). Preference is given to using ammonia in step B.

The ammonium salts are usually used as solids if appropriate with their typical contents of water of crystallization, and ammonia is usually used as gas. However, aqueous solutions can also be used if desired, in which case not only the water arising in the formation of the 4(1H)pyridinone derivative but also the water of the solution are removed by means of the entrainer in step B.

The ammonium salts are generally added in a molar ratio of ammonium ion:trione of from 3:1 to 12:1, preferably in a molar ratio of from 5:1 to 10:1.

The gaseous ammonia is introduced into the reaction mixture as a finely divided stream, e.g. through a frit, until a molar ratio of the total amount of ammonia:trione of from 6:1 to 14:1, preferably from 8:1 to 12:1, has been reached. The introduction of the ammonia gas can be carried out initially at temperatures or temperature profiles below reflux conditions or right from the start under the conditions of removal of the water of reaction, i.e. under reflux.

The crude product obtained in step B is usually worked up by distilling off the remaining $C_1$–$C_4$-alkanol, suspending the residue in water, filtering it off with suction, washing it with water and a little (!), optionally (ice) cooled, ethanol and finally drying it.

The pyridinone obtained in step B is reacted in step C with phosphorus oxide chloride ($POCl_3$) or with a mixture comprising phosphorus oxide chloride and at least one organic solvent selected from the group consisting of toluene, o-xylene, m-xylene and p-xylene. The reaction is generally carried out under reflux with boiling of the phosphorus oxide chloride or the mixture of phosphorus oxide chloride and organic solvent.

The molar ratio of pyridinone of the formula c to phosphorus oxide chloride is usually from 1:5 to 1:25, in particular from 1:8 to 1:20. If a mixture of phosphorus oxide chloride and organic solvent is used, the molar excess of phosphorus oxide chloride over the pyridinone can be reduced.

The molar ratio of phosphorus oxide chloride to the organic solvent is usually from 0.8:1 to 2:1, in particular from 1:1 to 1.5:1.

The crude product obtained in step C is normally worked up by removing (e.g. distilling off) the excess phosphorus oxide chloride or the mixture of phosphorus oxide chloride and organic solvent, dissolving the residue (ammonium salt!) in water, bringing the pH to 7 by adding concentrated alkali (e.g. sodium hydroxide solution, sodium carbonate solution) or a basic compound (e.g. sodium hydroxide, sodium carbonate), filtering off the resulting precipitate with suction, washing with water and finally drying the solid.

The present invention further provides a process for preparing $C_1$–$C_4$-alkyl pyridine-2-carboxylate derivatives of the formula a

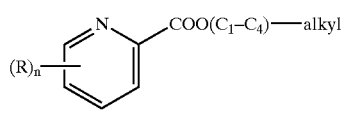
(a)

in which
R is hydrogen or a $C_1$–$C_{12}$-alkyl or $C_1$–$C_{12}$-alkoxy radical and
n is 0, 1, 2, 3 or 4,
by acid hydrolysis of a 2-cyanopyridine derivative of the formula a'

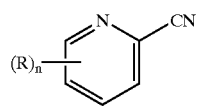
(a')

by means of an anhydrous inorganic acid or its anhydride in the presence of water and a $C_1$–$C_4$-alkanol, wherein an equimolar amount of water is added to the 2-cyanopyridine derivative of the formula a' prior to addition of the anhydrous inorganic acid or its anhydride.

Reaction conditions for this process have already been described under step A' of the process of the present invention for preparing terpyridines of the formula I from 2-cyanopyridine derivatives of the formula a' and apply analogously here.

The present invention also provides a process for preparing 1,5-bis(2-pyridyl)pentane-1,3,5-trione derivatives of the formula b

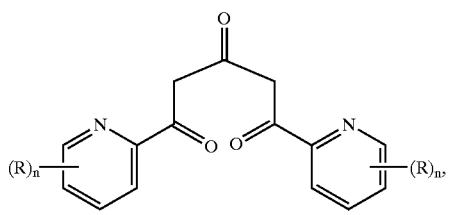
(b)

in which
R are hydrogens or identical $C_1$–$C_{12}$-alkyl or $C_1$–$C12$-alkoxy radicals and
n is 0, 1, 2, 3 or 4 and is the same for both sets of radicals R,
by condensation of the $C_1$–$C_4$-alkyl pyridine-2-carboxylate derivative of the formula a

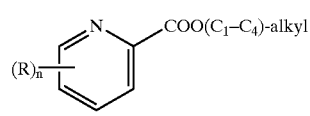
(a)

with acetone in an aprotic solvent in the presence of an alkali metal $C_1$–$C_4$-alkoxide or alkaline earth metal $C_1$–$C_4$-alkoxide as base.

Bases used are, in particular, alkali metal $C_1$–$C_4$-alkoxides, preferably sodium $C_1$–$C_4$-alkoxides and particularly preferably sodium methoxide.

Further reaction conditions for this process have been described under step A of the process of the present invention for preparing terpyridines of the formula I from 2-cyanopyridine derivatives of the formula a' and apply analogously here.

Furthermore, the present invention provides a process for preparing 2,6-bis(2-pyridyl)-4(1H)pyridinone derivatives of the formula c

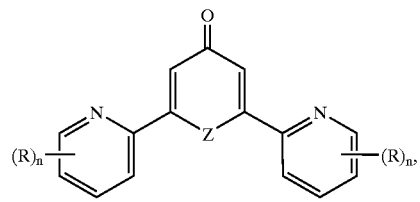
(c)

in which
R are hydrogens or identical $C_1$–$C_{12}$-alkyl or $C_1$–$C_{12}$-alkoxy radicals,
n is 0, 1, 2, 3 or 4 and is the same for both sets of radicals R,
Z is NH or $NH_2^{\ominus}[Y_{1/q}]^{\ominus}$ and
Y is the anion of a q-basic acid $H_qY$,
by reacting the 1,5-bis(2-pyridyl)pentane-1,3,5-trione derivative of the formula b

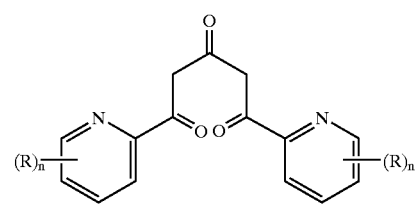
(b)

with ammonia or ammonium salts $(NH_4)_qY$ with removal of the water of reaction formed, wherein the removal of the water of reaction is carried out using a $C_1$–$C_4$-alkanol as entrainer.

As entrainer for removing the water of reaction, use is made, in particular, of ethanol, n-propanol, i-propanol or n-butanol, with preference being given to ethanol.

Further reaction conditions for this process have already been described under step B of the process of the present invention for preparing terpyridines of the formula I from 2-cyanopyridine derivatives of the formula a' and apply analogously here.

Also provided is a process for preparing terpyridines of the formula I

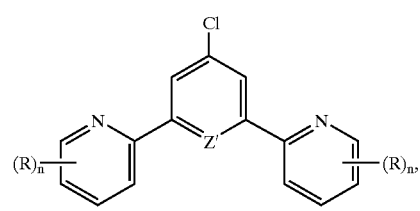
(I)

in which
R are hydrogens or identical $C_1$–$C_{12}$-alkyl or $C_1$–$C_{12}$-alkoxy radicals, n is 0, 1, 2, 3 or 4 and is the same for both sets of radicals
Z' is nitrogen or $NH^{\oplus}[Y_{1/q}]^{\ominus}$ and
Y is the acid anion of a q-basic acid $H_qY$,
by chlorination of the 2,6-bis(2-pyridyl)-4(1H)pyridinone derivative of the formula b

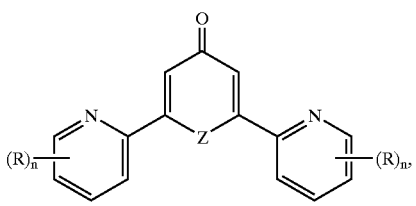

(b)

where Z is NH or $NH_2^{\oplus}[Y_{1/q}]^{\ominus}$,
wherein the chlorination is carried out using phosphorus oxide chloride ($POCl_3$) or using a mixture comprising phosphorus oxide chloride and at least one organic solvent selected from the group consisting of toluene, o-xylene, m-xylene and p-xylene.

Chlorinating agents which can be used are, in particular, phosphorus oxide chloride ($POCl_3$) or a mixture comprising phosphorus oxide chloride and toluene.

Further reaction conditions for this process have already been described under step C of the process of the present invention for preparing terpyridines of the formula I from 2-cyanopyridine derivatives of the formula a' and apply analogously here.

EXAMPLES

Reaction Step A':

In a 500 ml reaction vessel, 20.8 q (0.2 mol) of 2-cyanopyridine were dissolved in 300 ml of absolute ethanol. After addition of 3.6 g (0.2 mol) of water, the reaction mixture was heated to 40° C. About 60 g of hydrogen chloride gas were subsequently passed into the mixture over a period of 2 hours, resulting in a rise in the reaction temperature to 55° C. After about 45 minutes, a white precipitate formed. After introduction of hydrogen chloride was complete, the reaction mixture was heated to 80° C. and maintained at this temperature for an after-reaction time of 3 hours. The solvent was subsequently removed on a rotary evaporator, the residue was taken up in 50 ml of water and the pH was adjusted to 7.5 by means of sodium bicarbonate solution. The aqueous phase was extracted three times with 200 ml each time of ethyl acetate and the combined extracts were subsequently dried over sodium sulfate. After filtration and removal of the solvent on a rotary evaporator at 60° C./25 hPa, the ethyl pyridine-2-carboxylate remained as a colorless liquid. The yield was 28.2 g (93.4% of theory).

Reaction Step A:

A/1: Reaction of ethyl pyridine-2-carboxylate with acetone:

In a 1 l flask provided with a stirrer, a suspension of 19.5 g (362 mmol) of sodium methoxide in 160 ml of tetrahydrofuran (THF) was heated to reflux (about 66° C.) under a blanket of nitrogen. A solution of 37.9 g (251 mmol) of ethyl pyridine-2-carboxylate and 8.7 ml (6.9 g, 120 mmol) of acetone in 200 ml of THF was subsequently added dropwise over a period of 4 hours, the reaction mixture was refluxed for a further 1.5 hours and the THF was taken off under reduced pressure.

The orange-red solid which remained was dissolved in 450 ml of water and neutralized with 5% strength acetic acid, resulting in precipitation of a yellow solid.

The crystalline precipitate was filtered off with suction and washed with a little water and three times with 25 ml each time of cold ethanol.

Drying in a vacuum drying oven at 40° C. gave 23.9 g (74.6% of theory) of yellowish olive green crude product of the compound

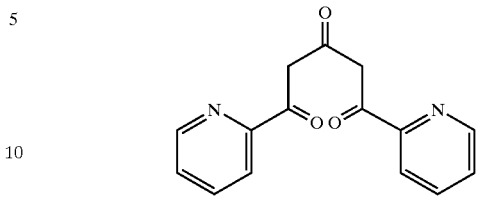

having a melting point of 92–94° C.

Recrystallization of a sample of the product from water/ethanol (150 ml: 250 ml) gave olive green crystals having a melting point of 99–100° C.

Recrystallization of 20 g of a sample of the product from n-hexane/ethanol (150 ml: 250 ml) gave 13 g of olive green crystals having a melting point of 101–102° C.

A/2: Reaction of Ethyl Pyridine-2-carboxylate with Acetone:

In a 4 l flask provided with a stirrer, a suspension of 195.4 g (3.617 mol) of sodium methoxide in 1000 ml of tetrahydrofuran (THF) was heated to reflux (about 66° C.) under a blanket of nitrogen. A solution of 379.3 g (2.514 mol) of ethyl pyridine-2-carboxylate and 92.3 ml (73.0 g, 1.257 mol) of acetone in 1000 ml of THF was subsequently added dropwise over a period of 4 hours, the reaction mixture was refluxed for a further 1.5 hours and the THF was taken off at 60° C./35 hPa.

The orange-red solid which remained was dissolved in 4000 ml of water and neutralized with about 5% strength acetic acid, resulting in precipitation of a yellow solid and formation of a thick suspension. The mixture was stirred for another hour, and the precipitate was then filtered off with suction and washed three times with 120 ml each time of water.

Drying in a vacuum drying oven at 50° C. gave 187 g (55.5% of theory) of olive green crude product of the compound

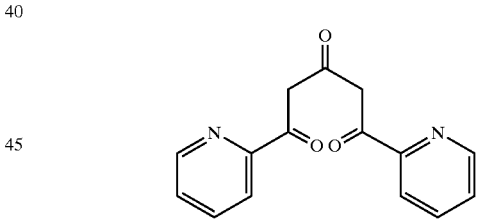

having a melting point of 91–92° C.

Reaction Step B:

B/1: Reaction of 1,5-bis(2-pyridyl)pentane-1,3,5-trione with ammonium formate:

In a 1 l flask provided with a stirrer, water separator and reflux condenser, a solution of 20.4 g (77.0 mmol) of 1,5-bis(2-pyridyl)pentane-1,3,5-trione and 34.0 g (539 mmol) of ammonium formate in 500 ml of absolute ethanol was refluxed at 79° C.

After the solution had been heated for 30 minutes, a total of about 350 ml of ethanol/water were separated off over a period of 6 hours. The dark brown reaction solution was allowed to stand overnight, allowed to cool to room temperature and evaporated to about 100 ml on a rotary evaporator.

The concentrate obtained was cooled in ice, the crystalline precipitate was filtered off with suction and washed twice with a little cold ethanol and twice with about 20 ml of water.

Drying in a vacuum drying oven at 50° C. gave 10 g (44.3% of theory) of light-brown, crystalline crude product of the compound

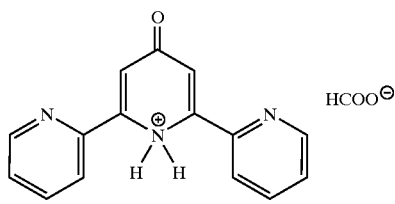

having a melting range of 104–114° C.

Recrystallization of a sample of the crude product from n-hexane/ethanol (1:2) gave light-beige crystals having a melting range of 120° C.–125° C.

B/2: Reaction of 1,5-bis(2-pyridyl)pentane-1,3,5-trione with ammonium acetate:

In a 2 l flask provided with a stirrer, water separator and reflux condenser, a solution of 61.1 g (231 mmol) of 1,5-bis(2-pyridyl)pentane-1,3,5-trione and 124.6 g (1.617 mol) of ammonium acetate in 1500 ml of absolute ethanol was refluxed at 78° C.

After the solution had been heated for 30 minutes, a total of about 1200 ml of ethanol/water were separated off over a period of 6 hours while the temperature was increased to a final temperature of 83° C. The dark brown reaction solution was allowed to stand over the weekend, allowed to cool to room temperature and evaporated to about 300 ml on a rotary evaporator.

The concentrate obtained was cooled in ice, and the crystalline precipitate was filtered off with suction and washed twice with a little cold ethanol.

Drying in a vacuum drying oven at 50° C. gave 53.5 g (75.46% of theory) of light-brown, crystalline crude product of the compound

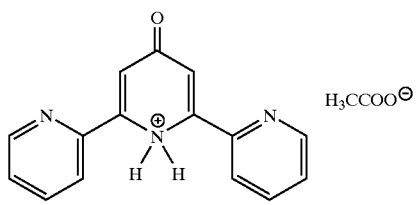

having a melting point of 128–131° C.

B/3: Reaction of 1,5-bis(2-pyridyl)pentane-1,3,5-trione with ammonium carbonate:

In a 2 l flask provided with a stirrer, water separator and reflux condenser, a solution of 40.8 g (154 mmol) of 1,5-bis(2-pyridyl)pentane-1,3,5-trione and 52.0 g (540 mmol) of ammonium carbonate in 1000 ml of absolute ethanol was refluxed at 72° C.

After the solution had been heated for 30 minutes, a total of about 700 ml of ethanol/water were separated off over a period of 6 hours while the temperature was increased to a final temperature of 79° C. During this procedure, a sublimate, presumably ammonium carbonate, was deposited in the water separator and condenser.

The dark brown reaction solution was allowed to stand overnight, allowed to cool to room temperature and evaporated on a rotary evaporator at 60° C./40 hPa. The dark, resinous residue was admixed with 200 ml of water, stirred and the crystalline mass formed was filtered off with suction, washed twice with 50 ml each time of water and once with 20 ml of cold ethanol.

Drying in a vacuum drying oven at 50° C. gave 29 g (75.6% of theory) of brown, crystalline crude product of the compound

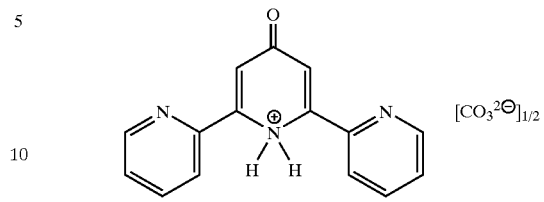

which displayed two melting ranges at 128–131° C. and 154–157° C.

Recrystallization of the crude product from a mixture of 300 ml of ethyl acetate and 50 ml of ethanol with cooling to −10° C. by means of an ice/sodium chloride mixture gave light-brown crystals which were filtered off with suction and dried at 50° C. in a vacuum drying oven. The yield was 8.8 g and the melting point was 167–169° C.

The filtrate from the recrystallization was concentrated on a rotary evaporator and taken up in 60 ml of ethanol. Cooling to −10° C. by means of an ice/sodium chloride mixture gave light-brown crystals which were filtered off with suction and dried at 50° C. in a vacuum drying oven. The yield from the secondary crystallization was 5.4 g and the melting point was 170–173° C.

Precipitation of the filtrate with n-hexane gave another 0.9 g of brown crystals which were likewise filtered off with suction and dried at 50° C. in a vacuum drying oven. The melting point of this fraction was 167–170° C.

The total yield of these three fractions was 15.1 g (39.4% of theory).

B/4: Reaction of 1,5-bis(2-pyridyl)pentane-1,3,5-trione with ammonium hydrogencarbonate:

In a 2 l flask provided with a stirrer, water separator and reflux condenser, a solution of 40.8 g (154 mmol) of 1,5-bis-(2-pyridyl)pentane-1,3,5-trione and 85.3 g (1.08 mol) of ammonium hydrogencarbonbate in 1000 ml of absolute ethanol was refluxed at 75° C.

After the solution had been heated for 30 minutes, a total of about 600 ml of ethanol/water were separated off over a period of 6 hours while the temperature was increased to a final temperature of 79° C. Once again, a sublimate, presumably ammonium (hydrogen)carbonate, deposited in the water separator and condenser.

The dark brown reaction solution was allowed to stand overnight, allowed to cool to room temperature and evaporated at 60° C./40 hPa on a rotary evaporator. The dark, resinous residue was admixed with 200 ml of water, stirred and the crystalline mass formed was filtered off with suction, washed twice with 30 ml each time of water and once with 20 ml of cold ethanol.

Drying in a vacuum drying oven at 50° C. gave 29.4 g (77.4% of theory) of brown, crystalline crude product of the compound

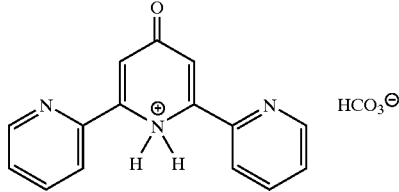

having a melting range of 147–156° C.

Recrystallization of the crude product from a mixture of 100 ml of n-hexane and 260 ml of ethanol with cooling to −10° C. by means of an ice/sodium chloride mixture gave beige/light-brown crystals which were filtered off with suction and dried at 50° C. in a vacuum drying oven. The yield was 14 g and the melting point was 169–172° C.

The filtrate from the recrystallization was concentrated to about 50 ml on a rotary evaporator and cooling to −10° C. by means of an ice/sodium chloride mixture gave light to medium brown crystals which were filtered off with suction and dried at 50° C. in a vacuum drying oven. The yield from the secondary crystallization was 6 g and the melting point was 169–172° C.

The total yield of the two fractions was 20 g (52.1% of theory).

B/5: Reaction of 1,5-bis(2-pyridyl)pentane-1,3,5-trione with Gaseous ammonia:

In a 4 l flask provided with a stirrer, water separator and reflux condenser, a solution of 174 g (0.649 mol) of 1,5-bis-(2-pyridyl)pentane-1,3,5-trione in 2000 ml of absolute ethanol was heated to 40° C. 77 g of ammonia gas were passed into the dark solution over a period of 3 hours while increasing the temperature to a final temperature of 55° C. The reaction mixture was heated to 57° C. and, while continuing to introduce a gentle stream of ammonia gas, about 1050 ml of ethanol/water were separated off over a period of 3 hours while increasing the temperature to a final temperature of 78° C. Toward the end of the removal of ethanol/water, another 103 g of ammonia gas were fed in.

The dark brown reaction solution was allowed to cool to room temperature while stirring and allowed to stand over the weekend. The remaining alcohol was then removed at 60° C./25 hPa on a rotary evaporator, the dark brown, crystalline residue was admixed with 800 ml of water, stirred at room temperature and allowed to stand overnight.

The crystalline mass was filtered off with suction, washed three times with 100 ml of water and twice with 30 ml each time of cold ethanol.

Drying in a vacuum drying oven at 50° C. gave 156.2 g of crude product of the compound

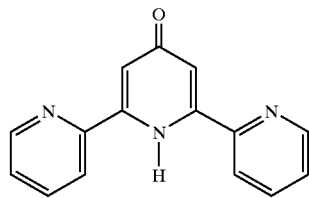

which, however, had a water content determined by the Karl Fischer method of 15.5% and a solids content determined by drying at 150° C. of 83.8%. Drying again at 50° C. in a vacuum drying oven finally gave 133 g of product having a solids content determined by drying at 150° C. of 90.6%. The yield was therefore about 80% of theory. The melting range was 153–158° C.

Reaction Step C:

C/1: Reaction of 2,6-bis(2-pyridyl)-4(1H)pyridinone with Phosphorus Oxide Chloride:

750 ml of phosphorus oxide chloride were placed in a 2 l flask provided with a stirrer and reflux condenser and, at room temperature, 140 g (0.561 mol) of the 2,6-bis(2-pyridyl)-4(1H)pyridinone obtained in reaction B/5 were added a little at a time. The reaction mixture was refluxed at about 107° C. for 7 hours, subsequently allowed to cool to room temperature and allowed to stand overnight.

The excess phosphorus oxide chloride was distilled off at 65° C./35 hPa, the dark mass which remained was broken up in a mortar, suspended in 300 ml of n-hexane and then filtered off with suction and washed with a little n-hexane.

Drying in a vacuum drying oven at 40° C. gave 248 g of solid which was dissolved in 2000 ml of water. The solution was heated to 35° C. and neutralized by addition of sodium carbonate a little at a time (vigorous foaming!). After stirring for one hour, the dark brown, crystalline precipitate was filtered off with suction, washed three times with 100 ml each time of water and dried at 50° C. in a vacuum drying oven. This gave 143 g of crude product of the compound

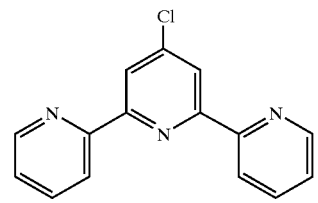

which had a melting point of 145–148° C.

Recrystallization of the crude product from 2500 ml of ethyl acetate with addition of activated carbon gave light-brown crystals which were filtered off with suction and dried at 50° C. in a vacuum drying oven. The yield was 57 g and the melting point was 150–152° C.

The filtrate from the recrystallization was concentrated to a volume of about 200 ml on a rotary evaporator, cooled in ice, the precipitate was filtered off, washed with a little ethyl acetate and dried at 50° C. in a vacuum drying oven. The yield from the secondary crystallization was 42.2 g and the melting point was 149–151° C.

The total yield of the two fractions was 99.2 g (66.1% of theory).

C/2: Reaction of 2,6-bis(2-pyridyl)-4(1H)pyridinone with a Phosphorus oxide chloride/toluene mixture:

14 g (46 mmol) of the 2,6-bis-(2-pyridyl)-4(1H) pyridinone $CH_3COOH$ obtained in reaction B/2 and a mixture of 50 ml of phosphorus oxide chloride with 50 ml of toluene were placed in a 500 ml flask provided with a stirrer and reflux condenser, heated to 103° C. and refluxed at this temperature for 5.5 hours. The mixture was subsequently allowed to cool to room temperature and allowed to stand overnight.

The phosphorus oxide chloride/toluene mixture was removed under reduced pressure on a rotary evaporator, the crystalline residue was dissolved in 300 ml of water and the solution was neutralized with solid sodium carbonate. This resulted in precipitation of a virtually white solid which was filtered off with suction and washed twice with 30 ml each time of water. Drying in a vacuum drying oven at 50° C. gave 10 g (82% of theory) of virtually colorless crude product of the compound

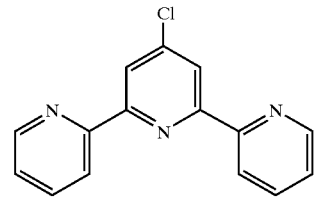

which had a melting point of 148–150° C.

We claim:

1. A process for preparing a terpyridine compound of the formula I

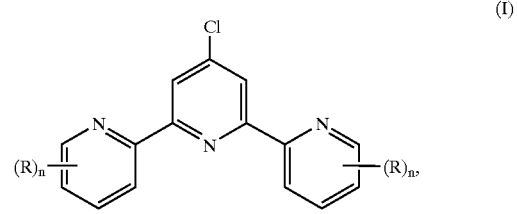

in which
R are hydrogens or identical $C_1$–$C_{12}$-alkyl or $C_1$–$C_{12}$-alkoxy radicals and
n is 0, 1, 2, 3 or 4 and is the same for both sets of radicals R, by successive reaction steps comprising
A) condensation of a $C_1$–$C_4$-alkyl pyridine-2-carboxylate derivative of the formula a

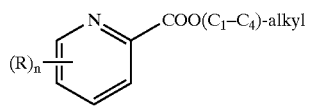

with acetone in an aprotic solvent in the presence of a base,
B) reaction of the 1,5-bis(2-pyridyl)pentane-1,3,5-trione derivative of the formula b

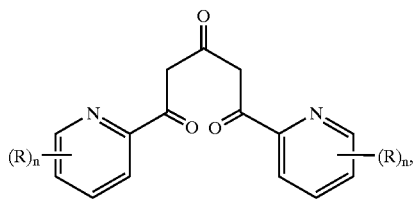

obtained in reaction step A with ammonia or ammonium salts $(NH_4)_qY$ with removal of the water of reaction formed, where the variable Y in $(NH_4)_qY$ is the anion of the parent q-basic acid $H_qY$ of the ammonium salt, and
C) chlorination of the 2,6-bis(2-pyridyl)-4(1H) pyridinone derivative of the formula c obtained in reaction step B,

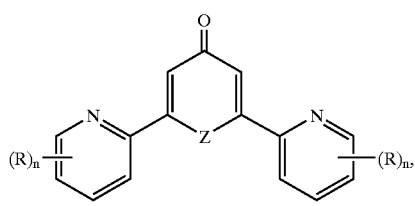

where Z is NH in the case of a reaction with ammonia in reaction step B and is $NH_2^\oplus[Y_{1/q}]^\ominus$ in the case of a reaction with ammonium salt $(NH_4)_qY$ in reaction step B,
wherein
the reaction step A is preceded by a reaction step A' in which the $C_1$–$C_4$-alkyl pyridine-2-carboxylate derivative of the formula a is obtained by
A') acid hydrolysis of a 2-cyanopyridine derivative of the formula a'

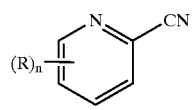

by means of an anhydrous inorganic acid or its anhydride in the presence of water and a $C_1$–$C_4$-alkanol, with an equimolar amount of water being added to the 2-cyanopyridine derivative of the formula a' prior to addition of the anhydrous inorganic acid or its anhydride,
the base used in reaction step A is an alkali metal $C_1$–$C_4$-alkoxide or alkaline earth metal $C_1$–$C_4$-alkoxide, the removal of the water of reaction in reaction step B is carried out using a $C_1$–$C_4$-alkanol as entrainer
and
the chlorination of the 2,6-bis(2-pyridyl)-4(1H) pyridinone derivative of the formula c in reaction step C is carried out using phosphorus oxide chloride ($POCl_3$) or using a mixture comprising phosphorus oxide chloride and at least one organic solvent selected from the group consisting of toluene, o-xylene, m-xylene and p-xylene.

2. A process as claimed in claim 1, wherein the base used in reaction step A is an alkali metal $C_1$–$C_4$-alkoxide.

3. A process as claimed in claim 1, wherein the base used in reaction step A is sodium $C_1$–$C_4$-alkoxide.

4. A process as claimed in claim 1, wherein the base used in reaction step A is sodium ethoxide.

5. A process as claimed in claim 1, wherein the removal of the water of reaction in reaction step B is carried out using ethanol, n-propanol, i-propanol or n-butanol as entrainer.

6. A process as claimed in claim I, wherein the removal of the water of reaction in reaction step B is carried out using ethanol as entrainer.

7. A process as claimed in claim 1, wherein the chlorination of the 2,6-bis(2-pyridyl)-4(1H)pyridinone derivative of the formula b is carried out using phosphorus oxide chloride ($POCl_3$) or using a mixture comprising phosphorus oxide chloride and toluene.

8. A process for preparing a terpyridine compound of the formula I

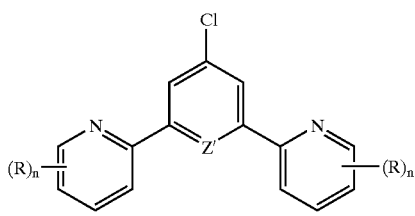

in which
R are hydrogens or identical $C_1$–$C_{12}$-alkyl or $C_1$–$C_{12}$-alkoxy radicals,
n is 0, 1, 2, 3 or 4 and is the same for both sets of radicals R,
Z' is nitrogen or $NH_2^\oplus[Y_{1/q}]^\ominus$ and
Y is the acid anion of a q-basic acid $H_qY$,
by chlorination of the 2,6-bis(2-pyridyl)-4(1H)pyridinone derivative of the formula b

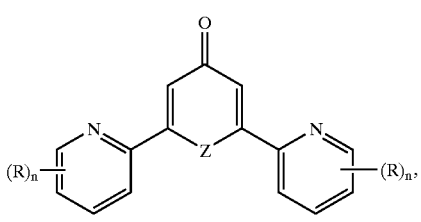

where Z is NH or $NH_2^\oplus[Y_{1/q}]^\ominus$,
wherein the chlorination is carried out using phosphorus oxide chloride ($POCl_3$) or using a mixture comprising phosphorus oxide chloride and at least one organic solvent selected from the group consisting of toluene, o-xylene, m-xylene and p-xylene.

9. A process as claimed in claim 8, wherein the chlorination is carried out using phosphorus oxide chloride ($POCl_3$) or using a mixture comprising phosphorus oxide chloride and toluene.

* * * * *